United States Patent
Pan et al.

(10) Patent No.: US 10,629,050 B2
(45) Date of Patent: Apr. 21, 2020

(54) ACCIDENTAL TUMBLING MONITORING METHOD, SYSTEM AND TERMINAL

(71) Applicant: FUJIAN UNIVERSITY OF TECHNOLOGY, Fuzhou, Fujian (CN)

(72) Inventors: Zhengxiang Pan, Fujian (CN); Fumin Zou, Fujian (CN); Xinhua Jiang, Fujian (CN); Junmin Wang, Fujian (CN); Xiaosheng Huang, Fujian (CN); Lvchao Liao, Fujian (CN); Zhenhua Gan, Fujian (CN); Hongtu Lai, Fujian (CN); Quan Zhu, Fujian (CN); Weidong Fang, Fujian (CN); Xiang Xu, Fujian (CN); Rong Hu, Fujian (CN); Shuling Zhang, Fujian (CN); Zibiao Chen, Fujian (CN)

(73) Assignee: FUJIAN UNIVERSITY OF TECHNOLOGY, Fuzhou (CN)

( * ) Notice: Subject to any disclaimer, the term of this patent is extended or adjusted under 35 U.S.C. 154(b) by 0 days.

(21) Appl. No.: 16/336,930

(22) PCT Filed: Dec. 12, 2016

(86) PCT No.: PCT/CN2016/109372
§ 371 (c)(1),
(2) Date: Mar. 27, 2019

(87) PCT Pub. No.: WO2018/058790
PCT Pub. Date: Apr. 5, 2018

(65) Prior Publication Data
US 2020/0035081 A1    Jan. 30, 2020

(30) Foreign Application Priority Data

Sep. 30, 2016  (CN) .......................... 2016 1 0870609

(51) Int. Cl.
*G08B 21/04* (2006.01)
*A43B 3/00* (2006.01)

(52) U.S. Cl.
CPC ........ *G08B 21/0446* (2013.01); *A43B 3/0005* (2013.01); *G08B 21/043* (2013.01)

(58) Field of Classification Search
CPC .............. G08B 21/043; G08B 21/0446; G08B 21/048; A43B 3/0005; A43B 7/00;
(Continued)

(56) References Cited

U.S. PATENT DOCUMENTS

| | | | |
|---|---|---|---|
| 2009/0099113 A1* | 4/2009 | Jimenez ............. | C12N 15/1137 514/44 R |
| 2009/0247909 A1* | 10/2009 | Mukumoto .............. | A43B 7/28 600/592 |
| 2013/0000156 A1* | 1/2013 | Andoh ................. | A43B 3/0005 36/136 |

FOREIGN PATENT DOCUMENTS

| CN | 103405001 A | 11/2013 |
|---|---|---|
| CN | 103581852 A | 2/2014 |

(Continued)

OTHER PUBLICATIONS

International search report of PCT Patent Application No. PCT/CN2016/109372 dated Jun. 27, 2017.

*Primary Examiner* — Van T Trieu

(57) ABSTRACT

An accidental tumbling monitoring method, system and a terminal are disclosed. When a human wearing intelligent shoes is in an accidental tumbling state, whether or not a first inclination angle of soles of the intelligent shoes is restored to a preset inclination range within a first preset time range is determined. If the human tumbles seriously, positioning information of the human wearing the intelligent shoes is sent to a guardian, whether or not a monitoring platform receives feedback information from the guardian within a (Continued)

second preset time range is determined, if not, the monitoring platform sends first aid information of the human wearing the intelligent shoes to an emergency center, and therefore, the situation that the human wearing the intelligent shoes has an accident due to belated treatment is avoided.

10 Claims, 2 Drawing Sheets

(58) Field of Classification Search
CPC ..... A43B 7/1455; A61B 5/103; A61B 5/1036;
A61B 5/111; A61B 5/112; A61B 5/117;
A61B 5/1121; A61B 5/1122; A61B
5/1123; A61B 22/0023
See application file for complete search history.

(56) References Cited

FOREIGN PATENT DOCUMENTS

| CN | 104041983 | * | 3/2014 | |
|---|---|---|---|---|
| CN | 105185037 A | | 12/2015 | |
| CN | 105678958 A | | 6/2016 | |
| CN | 105796112 A | | 7/2016 | |
| CN | 106408870 A | * | 2/2017 | ......... G08B 21/0446 |

* cited by examiner

Step 1: Obtain, when receiving information that a human wearing intelligent shoes is in an accidental tumbling state, a first inclination angle of soles of the intelligent shoes and positioning information;

↓

Step 2: Determine whether or not the first inclination angle is restored to a preset inclination angle range within a first preset time range;

↓

Step 3: If not, send the positioning information to a guardian, and if a monitoring platform does not receive feedback information from the guardian within a second preset time range, the monitoring platform sends first aid information to an emergency center; or if yes; obtain the speed value of the intelligent shoes, and if the speed value is less than a preset speed threshold, send the positioning information to the guardian.

FIG. 1

ACCIDENTAL TUMBLING MONITORING METHOD, SYSTEM AND TERMINAL

TECHNICAL FIELD

The invention relates to the field of intelligent monitoring, in particular to an accidental tumbling monitoring method, system and terminal.

DESCRIPTION OF RELATED ART

In recent years, due to the gradual increase of aged populations, population aging has become a great challenge in nowadays society, and construction and perfection of intelligent old-age systems are extremely urgent. In addition, the increase of the working pressure of young people and the acceleration of the living tempo usually lead to lacking in care for the aged or real-time attendance to the aged. In daily life, the aged may tumble accidentally or even faint when suffering from a cerebral thrombosis, myocardial infarction or other accidents, and in this case, belated treatment may result in exacerbation or even death of the aged.

To solve the above problems, monitoring devices used for monitoring accidental tumbling of the aged, such as smart watches, have appeared on the present market and can give out an alarm signal to a guardian when the aged tumbles accidentally. However, in actual use, it is possible that the aged just tumbles slightly and can still normally walk, but in this case, the smart watches still give an alarm, which causes a false alarm.

Technical Issue

The technical issue to be settled by the invention is to provide an accidental tumbling monitoring method, system and a terminal for a human wearing intelligent shoes.

Solutions to the Technical Issue

Technical Solutions

A first technical solution adopted by the invention to settle the above technical issue is as follows:

An accidental tumbling monitoring method comprises:

Step 1, obtaining, when receiving information that a human wearing intelligent shoes is in an accidental tumbling state, a first inclination angle of soles of the intelligent shoes and positioning information;

Step 2, determining whether or not the first inclination angle is restored to a preset inclination angle range within a first preset time range; and Step 3, if not, sending the positioning information to a guardian; and if a monitoring platform does not receive feedback information from the guardian within a second preset time range, sending first aid information to an emergency center by the monitoring platform; or if yes, obtaining the speed value of the intelligent shoes, and if the speed value is less than a preset speed threshold, sending the positioning information to the guardian.

A second technical solution adopted by the invention is as follows:

An accidental tumbling monitoring system comprises a first acquisition module, a first determination module and a first processing module, wherein:

The first acquisition module is used for obtaining, when receiving information that a human wearing intelligent shoes is in an accidental tumbling state, a first inclination angle of soles of the intelligent shoes and positioning information;

The first determination module is used for determining whether or not the first inclination angle is restored to a preset inclination angle range within a first preset time range;

The first processing module comprises a first communication unit, a first acquisition unit and a second communication unit;

The first communication unit is used for sending the positioning information to a guardian if the first inclination angle is not restored to the preset inclination angle range within the first preset time range, and a monitoring platform sends first aid information to an emergency center if not receiving feedback information from the guardian within a second preset time range;

The first acquisition unit is used for obtaining the speed value of the intelligent shoes if the first inclination angle is restored to the preset inclination angle range within the first preset time range;

The second communication unit is used for sending the positioning information to the guardian if the speed value is less than a preset speed threshold.

A third technical solution adopted by the invention is as follows:

An accidental tumbling monitoring terminal comprises intelligent shoes, wherein gyro sensors, speed sensors, processors, positioning devices and communication devices are arranged in the intelligent shoes, and the gyro sensors, the speed sensors, the positioning devices and the communication devices are connected to the processors.

The gyro sensors are used for obtaining, when receiving information that a human wearing the intelligent shoes is in an accidental tumbling state, a first inclination angle of soles of the intelligent shoes.

The speed sensors are used for obtaining the speed value of the intelligent shoes if the first inclination angle is restored to the preset inclination angle range within the first preset time range.

The positioning devices are used for obtaining, when receiving information that the human wearing the intelligent shoes is in an accidental tumbling state, positioning information of the soles of the intelligent shoes.

The processors are used for determining whether or not the first inclination angle is restored to the preset inclination angle range within the first preset time range.

The communication devices are used for sending the positioning information to a guardian if the first inclination angle is not restored to the preset inclination angle range within the first preset time range.

Beneficial Effects of the Invention

Beneficial Effects

The accidental tumbling monitoring method, system and terminal of the invention have the following beneficial effects: when the human wearing the intelligent shoes is in an accidental tumbling state, whether or not the first inclination angle of the soles of the intelligent shoes is restored to the preset inclination range within the first preset time range is determined, wherein the preset inclination range represents an inclination angle range of the soles of the intelligent shoes during a normal walking process, the serious degree of accidental tumbling of the human wearing the intelligent shoes is determined in combination with the speed value of the intelligent shoes, and therefore, a false alarm is avoided. If the human tumbles seriously, the positioning information of the human wearing the intelligent shoes is sent to the guardian, and whether or not the monitoring platform receives feedback information from the guardian within the second preset time range is determined; if not, it indicates that guardian fails to offer aid in time, and the monitoring platform sends first aid information of the human wearing the intelligent shoes to an emergency center, in this way, accidental tumbling of the human wearing the intelligent shoes is deeply monitored, and the situation that the human wearing the intelligent shoes has an accident due to belated treatment is avoided.

BRIEF DESCRIPTION OF DRAWINGS

Figure 2:
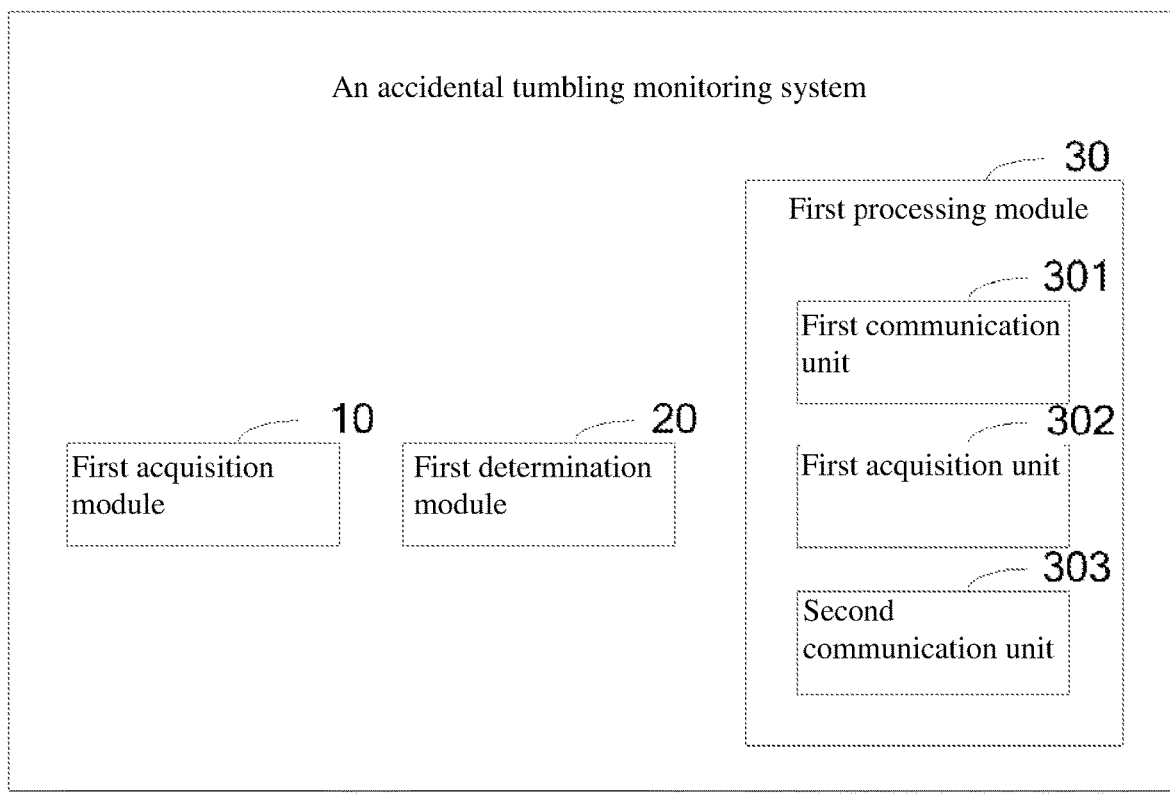

Brief Description of the Several Views of the Drawings

FIG. 1 is a step flow diagram of an accidental tumbling monitoring method of the invention;

FIG. 2 is a structural view of an accidental tumbling monitoring system of the invention;

REFERENCE SIGNS 10, first acquisition module; 20, first determination module; 30, first processing module; 301, first communication unit; 302, first acquisition unit; 302, second communication unit.

EMBODIMENTS OF THE INVENTION

Detailed Description of the Invention

The key conception of the invention lies in that: when information that a human wearing intelligent shoes is in an accidental tumbling state is received, whether or not a first inclination angle of soles of the intelligent shoes is restored to a preset inclination range within a first preset time range is determined, and the serious degree of accidental tumbling of the human wearing the intelligent shoes is determined in combination with the speed value of the intelligent shoes, so that a false alarm is avoided, and a first-aid alarm service is rapidly and accurately provided according to the severity of injuries.

Referring to FIG. 1, the invention provides an accidental tumbling monitoring method comprising:

Step 1, obtaining, when receiving information that a human wearing intelligent shoes is in an accidental tumbling state, a first inclination angle of soles of the intelligent shoes and positioning information;

Step 2, determining whether or not the first inclination angle is restored to a preset inclination angle range within a first preset time range; and Step 3, if not, sending the positioning information to a guardian, and if a monitoring platform does not receive feedback information from the guardian within a second preset time range, sending first aid information to an emergency center by the monitoring platform; or If yes, obtaining the speed value of the intelligent shoes, and if the speed value is less than a preset speed threshold, sending the positioning information to the guardian.

From the above description, the accidental tumbling monitoring method of the invention has the following beneficial effects: When the human wearing the intelligent shoes is in an accidental tumbling state, whether or not the first inclination angle of the soles of the intelligent shoes is restored to the preset inclination range within the first preset time range is determined, wherein the preset inclination range represents an inclination angle range of the soles of the intelligent shoes during a normal walking process, the serious degree of accidental tumbling of the human wearing the intelligent shoes is determined in combination with the speed value of the intelligent shoes, and therefore, a false alarm is avoided. If the human tumbles seriously, the positioning information of the human wearing the intelligent shoes is sent to the guardian, and whether or not the monitoring platform receives feedback information from the guardian within the second preset time range is determined; if not, it indicates that guardian fails to offer aid in time, and the monitoring platform sends first aid information of the human wearing the intelligent shoes to an emergency center, in this way, accidental tumbling of the human wearing the intelligent shoes is deeply monitored, and the situation that the human wearing the intelligent shoes has an accident due to belated treatment is avoided.

Furthermore, in Step 1, 'information that a human wearing intelligent shoes is in an accidental tumbling state' is determined through the following sub-steps:

Obtaining a pressure value of the soles of the intelligent shoes, and if the pressure value is less than a first pressure value, obtaining second inclination angles of the soles of the intelligent shoes, wherein the first pressure value of the intelligent shoes is obtained when the human wearing the intelligent shoes stands; and If at least one of the second inclination angles of the soles of the intelligent shoes is out of the preset inclination angle range, and the intelligent shoes have a continuous movement acceleration in an original direction within a third preset time, confirming that the human wearing intelligent shoes is in an accidental tumbling state.

From the above description, when the pressure value of the intelligent shoes falls between zero and the first pressure value (if the pressure value is zero, it indicates that the human does not wear an intelligent device used for obtaining the pressure value; if the pressure value reaches the first pressure value, it indicates the human wearing the intelligent shoes is in a standing state), the human wearing the intelligent shoes is in a sitting state or in a tumbling state, and then whether the human wearing the intelligent shoes is in the sitting state or in the tumbling state is further determined in combination with the inclination angles of the soles of the intelligent shoes by determining whether or not the intelligent shoes have a continuous movement acceleration in the original direction; if at least one of the second inclination angles of the soles of the intelligent shoes is out of the preset inclination angle range, it indicates that the human wearing the intelligent shoes sits with the legs crossed or tumbles; and furthermore, if the intelligent shoes still have a continuous movement acceleration in the original direction within a second preset time, it is confirmed that the human wearing the intelligent shoes is in the accidental tumbling state.

Furthermore, Step 1 further comprises the following sub-steps:

Obtaining direction data and acceleration data of the intelligent shoes, and then sending the direction data, the acceleration data and the first inclination angle to the monitoring platform to be recorded; and Simulating a dynamic model by the monitoring platform according to the direction data, the acceleration data and the first inclination angle received by the monitoring platform.

From the above description, at the moment the human wearing the intelligent shoes tumbles, the direction data, the acceleration data and the first inclination angle of the intelligent shoes are obtained and are sent to the monitoring platform to be recorded; the specific reason for the tumbling of the human wearing the intelligent shoes can be analyzed in the later stage by simulating and speculating the general tumbling situation of the human wearing the intelligent shoes at that moment according to the direction data, the acceleration data and the first inclination angle recorded in the monitoring platform, so that the tumbling process of the human wearing the intelligent shoes is visualized, and great assistance is provided for medical diagnosis.

Furthermore, Step 3 comprises the following sub-step:

Obtaining image data around the intelligent shoes, and then sending the image data to the guardian.

From the above description, when the human wearing the intelligent shoes is in a tumbling state, the image data round the human wearing the intelligent shoes are obtained, wherein the image data contain a landmark building near the position where the human wearing the intelligent shoes tumbles; and based on positioning by the positioning devices, the positioning accuracy can be improved with reference to the image data. Particularly, the approximate distance between a photographing position and the building can be worked out according to the building acquired from an image and the focal length and image resolution of cameras, and therefore, the positioning accuracy is improved.

Referring to FIG. 2, the invention further provides an accidental tumbling monitoring system. The accidental tumbling monitoring system comprises a first acquisition module 10, a first determination module 20 and a first processing module 30, wherein:

The first acquisition module 10 is used for obtaining, when receiving information that a human wearing intelligent shoes is in an accidental tumbling state, a first inclination angle of soles of the intelligent shoes and positioning information;

The first determination module 20 is used for determining whether or not the first inclination angle is restored to a preset inclination angle range within a first preset time range;

The first processing module 30 comprises a first communication unit 301, a first acquisition unit 302 and a second communication unit 303;

The first communication unit 301 is used for sending the positioning information to a guardian if the first inclination angle is not restored to the preset inclination angle range within the first preset time range, and a monitoring platform sends first aid information to an emergency center if not receiving feedback information from the guardian within a second preset time range;

The first acquisition unit 302 is used for obtaining the speed value of the intelligent shoes if the first inclination angle is restored to the preset inclination angle range within the first preset time range;

The second communication unit 303 is used for sending the positioning information to the guardian if the speed value is less than a preset speed threshold.

From the above description, the accidental tumbling monitoring system of the invention has the following beneficial effects: when the human wearing the intelligent shoes is in an accidental tumbling state, whether or not the first inclination angle of the soles of the intelligent shoes is restored to the preset inclination range within the first preset time range is determined, wherein the preset inclination range represents an inclination angle range of the soles of the intelligent shoes during a normal walking process, the serious degree of accidental tumbling of the human wearing the intelligent shoes is determined in combination with the speed value of the intelligent shoes, and therefore, a false alarm is avoided. If the human tumbles seriously, the positioning information of the human wearing the intelligent shoes is sent to the guardian, and whether or not the monitoring platform receives feedback information from the guardian within the second preset time range is determined; if not, it indicates that guardian fails to offer aid in time, and the monitoring platform sends first aid information of the human wearing the intelligent shoes to an emergency center, in this way, accidental tumbling of the human wearing the intelligent shoes is deeply monitored, and the situation that the human wearing the intelligent shoes has an accident due to belated treatment is avoided.

Furthermore, the first acquisition module particularly comprises a second acquisition unit, a third acquisition unit and a confirmation unit, wherein:

The second acquisition unit is used for obtaining a pressure value of the soles of the intelligent shoes;

The third acquisition unit is used for obtaining second inclination angles of the soles of the intelligent shoes if the pressure value is less than a first pressure value, wherein the first pressure value of the intelligent shoes is obtained when the human wearing the intelligent shoes stands;

The confirmation unit is used for conforming that the human wearing the intelligent shoes is in an accidental tumbling state when at least one of the second inclination angles of the soles of the intelligent shoes is out of the preset inclination angle range and the intelligent shoes have a continuous movement acceleration in an original direction within a third preset time range.

From the above description, when the pressure value of the intelligent shoes falls between zero and the first pressure value (if the pressure value is zero, it indicates that the human does not wear an intelligent device used for obtaining the pressure value; if the pressure value reaches the first pressure value, it indicates the human wearing the intelligent shoes is in a standing state), the human wearing the intelligent shoes is in a sitting state or in a tumbling state, and then whether the human wearing the intelligent shoes is in the sitting state or in the tumbling state is further determined in combination with the inclination angles of the soles of the intelligent shoes by determining whether or not the intelligent shoes have a continuous movement acceleration in the original direction; if at least one of the second inclination angles of the soles of the intelligent shoes is out of the preset inclination angle range, it indicates that the human wearing the intelligent shoes sits with the legs crossed or tumbles; and furthermore, if the intelligent shoes still have a continuous movement acceleration in the original direction within a second preset time, it is confirmed that the human wearing the intelligent shoes is in the accidental tumbling state.

Furthermore, the first acquisition module further comprises a fourth acquisition unit and a third communication unit, wherein:

The fourth acquisition unit is used for obtaining direction data and acceleration data of the intelligent shoes;

The third communication unit is used for sending the direction data, the acceleration data and the first inclination angle to a monitoring platform to be recorded.

The accidental tumbling monitoring system further comprises the monitoring platform used for simulating a dynamic model according to the received direction data, acceleration data and first inclination angle.

From the above description, at the moment the human wearing the intelligent shoes tumbles, the direction data, the acceleration data and the first inclination angle of the intelligent shoes are obtained and are sent to the monitoring platform to be recorded; the specific reason for the tumbling of the human wearing the intelligent shoes can be analyzed in the later stage by simulating and speculating the general tumbling situation of the human wearing the intelligent shoes at that moment according to the direction data, the acceleration data and the first inclination angle recorded in the monitoring platform, so that the tumbling process of the human wearing the intelligent shoes is visualized, and great assistance is provided for medical diagnosis.

Furthermore, the first processing module comprises a fifth acquisition unit and a fourth communication unit, wherein:

The fifth acquisition unit is used for obtaining image data around the intelligent shoes;

The fourth communication unit is used for sending the image data to the guardian.

From the above description, when the human wearing the intelligent shoes is in a tumbling state, the image data round the human wearing the intelligent shoes are obtained, wherein the image data contain a landmark building near the position where the human wearing the intelligent shoes tumbles; and based on positioning by the positioning devices, the positioning accuracy can be improved with reference to the image data. Particularly, the approximate distance between a photographing position and the building can be worked out according to the building acquired from an image and the focal length and image resolution of cameras, and therefore, the positioning accuracy is improved.

The invention further provides an accidental tumbling monitoring terminal. The accidental tumbling monitoring terminal comprises intelligent shoes, wherein gyro sensors, speed sensors, processors, positioning devices and communication devices are arranged in the intelligent shoes, and the gyro sensors, the speed sensors, the positioning devices and the communication devices are connected to the processors.

The gyro sensors are used for obtaining, when receiving information that a human wearing the intelligent shoes is in an accidental tumbling state, a first inclination angle of soles of the intelligent shoes;

The speed sensors are used for obtaining the speed value of the intelligent shoes if the first inclination angle is restored to a preset inclination angle range within a first preset time range;

The positioning devices are used for obtaining, when receiving the information that the human wearing the intelligent shoes is in an accidental tumbling state, positioning information of the soles of the intelligent shoes;

The processors are used for determining whether or not the first inclination angle is restored to the preset inclination angle range within the first preset time range;

The communication devices are used for sending the positioning information to a guardian if the first inclination angle is not restored to the preset inclination angle range within the first preset time range.

According to the accidental tumbling monitoring terminal, when it is confirmed by the processors in the terminal (intelligent shoes) that the human wearing the intelligent shoes is in an accidental tumbling state, whether or not the first inclination angle of the soles of the intelligent shoes obtained by the gyro sensors is restored to the preset inclination angle range within the first preset time range is determined, the serious degree of accidental tumbling of the human wearing the intelligent shoes is determined in combination with the speed value of the intelligent shoes, and therefore, a false alarm is avoided.

Furthermore, cameras connected to the processors are further arranged in the intelligent shoes and are used for obtaining image data around the intelligent shoes and sending the image data to the guardian. Positioning devices connected to the processors are further arranged in the intelligent shoes and are used for obtaining positioning information of the intelligent shoes.

From the above description, when the human wearing the intelligent shoes is in a tumbling state, the image data round the human wearing the intelligent shoes are obtained by the cameras, wherein the image data contain a landmark building near the position where the human wearing the intelligent shoes tumbles; and based on positioning by the positioning devices, the positioning accuracy can be improved with reference to the image data. Particularly, the approximate distance between a photographing position and the building can be worked out according to the building acquired from an image and the focal length and image resolution of the cameras, and therefore, the positioning accuracy is improved.

Referring to FIGS. 1-2, embodiment 1:

An accidental tumbling monitoring method comprises the following steps:

Step 1, when information that a human wearing intelligent shoes is in an accidental tumbling state, a first inclination angle of soles of the intelligent shoes and positioning information are obtained; direction data and acceleration data of the intelligent shoes are obtained at the same time, and the direction data, the acceleration data and the first inclination angle are sent to a monitoring platform to be recoded; and the monitoring platform simulates a dynamic model according to the received direction data, acceleration data and first inclination angle. At the moment the human wearing the intelligent shoes tumbles, the direction data, the acceleration data and the first inclination angle of the intelligent shoes are obtained and are sent to the monitoring platform to be recorded; the specific reason for the tumbling of the human wearing the intelligent shoes can be analyzed in the later stage by simulating and speculating the general tumbling situation of the human wearing the intelligent shoes at that moment according to the direction data, the acceleration data and the first inclination angle recorded in the monitoring platform, so that the tumbling process of the human wearing the intelligent shoes is visualized, and great assistance is provided for medical diagnosis.

Wherein, 'information that a human wearing intelligent shoes is in an accidental tumbling state' is determined through the following sub-steps:

A pressure value of the soles of the intelligent shoes is obtained; if the pressure value is less than a first pressure value, second inclination angles of the soles of the intelligent shoes are obtained, wherein the first pressure value of the intelligent shoes is obtained when the human wearing the intelligent shoes stands;

If at least one of the second inclination angles of the soles of the intelligent shoes is out of a preset inclination angle range, and the intelligent shoes have a continuous movement acceleration in an original direction within a third preset time range, it is confirmed that the human wearing the intelligent shoes is in an accidental tumbling state.

When the pressure value of the intelligent shoes falls between zero and the first pressure value (if the pressure value is zero, it indicates that the human does not wear an intelligent device used for obtaining the pressure value; if the pressure value reaches the first pressure value, it indicates the human wearing the intelligent shoes is in a standing state), the human wearing the intelligent shoes is in a sitting state or in a tumbling state, and then whether the human wearing the intelligent shoes is in the sitting state or in the tumbling state is further determined in combination with the inclination angles of the soles of the intelligent shoes by determining whether or not the intelligent shoes have a continuous movement acceleration in the original direction; if at least one of the second inclination angles of the soles of the intelligent shoes is out of the preset inclination angle range, it indicates that the human wearing the intelligent shoes sits with the legs crossed or tumbles; and furthermore, if the intelligent shoes still have a continuous movement acceleration in the original direction within a second preset time, it is confirmed that the human wearing the intelligent shoes is in the accidental tumbling state.

Step 2, whether or not the first inclination angle is restored to a preset inclination angle range within a first preset time range is determined, wherein the preset inclination angle range represents an included angle formed between the soles of the intelligent shoes and the horizontal plane and is 45°-90°.

Step 3, if the first inclination angle is not restored to the preset inclination angle range within the first preset time range, it indicates that the human wearing the intelligent shoes tumbles seriously, and at this moment, the positioning information of the human wearing the intelligent shoes is sent to a guardian; if the monitoring platform does not receive feedback information from the guardian within a second preset time range, it indicates that the guardian fails to rescue the human wearing the intelligent shoes in time, and in this case, the monitoring platform sends first aid information to an emergency center, so that the emergency center can provide a first aid service for the human wearing the intelligent shoes. In this way, accidental tumbling of the human wearing the intelligent shoes is deeply monitored, and the situation that the human wearing the intelligent shoes has an accident due to belated treatment is avoided; or If the first inclination angle is restored to the preset inclination angle range within the first preset time range, the speed value of the intelligent shoes is obtained; if the speed value is less than a preset speed threshold, it indicates that the human wearing the intelligent shoes tumbles, but still can walk slowly, and the positioning information is sent to the guardian. In the invention, the preset speed threshold is 3 km/h, and different speed thresholds can be set when human bodies at different ages and under different physical conditions wear the intelligent shoes.

Image data round the intelligent shoes are obtained at the same time and are sent to the guardian. When the human wearing the intelligent shoes is in a tumbling state, the image data round the human wearing the intelligent shoes are obtained, wherein the image data contain a landmark building near the position where the human wearing the intelligent shoes tumbles; and based on positioning by the positioning devices, the positioning accuracy can be improved with reference to the image data. Particularly, the approximate distance between a photographing position and the building can be worked out according to the building acquired from an image and the focal length and image resolution of cameras, and therefore, the positioning accuracy is improved.

According to the accidental tumbling monitoring method, system and terminal, when the human wearing the intelligent shoes is in an accidental tumbling state, whether or not the first inclination angle of the soles of the intelligent shoes is restored to the preset inclination range within the first preset time range is determined, wherein the preset inclination range represents an inclination angle range of the soles of the intelligent shoes during a normal walking process, the serious degree of accidental tumbling of the human wearing the intelligent shoes is determined in combination with the speed value of the intelligent shoes, and therefore, a false alarm is avoided. If the human tumbles seriously, the positioning information of the human wearing the intelligent shoes is sent to the guardian, and whether or not the monitoring platform receives feedback information from the guardian within the second preset time range is determined; if not, it indicates that guardian fails to offer aid in time, and the monitoring platform sends first aid information of the human wearing the intelligent shoes to an emergency center, in this way, accidental tumbling of the human wearing the intelligent shoes is deeply monitored, and the situation that the human wearing the intelligent shoes has an accident due to belated treatment is avoided.

The invention claimed is:

1. An accidental tumbling monitoring method, comprising:
   step 1, obtaining, when receiving information that a human wearing intelligent shoes is in an accidental tumbling state, a first inclination angle of soles of the intelligent shoes and positioning information;
   step 2, determining whether or not the first inclination angle is restored to a preset inclination angle range within a first preset time range; and
   step 3, if not, sending the positioning information to a guardian; and if a monitoring platform does not receive feedback information from the guardian within a second preset time range, sending first aid information to an emergency center by the monitoring platform; or
   if yes, obtaining a speed value of the intelligent shoes, and if the speed value is less than a preset speed threshold, sending the positioning information to the guardian.

2. The accidental tumbling monitoring method according to claim 1, wherein in Step 1, 'information that a human wearing intelligent shoes is in an accidental tumbling state' is determined through the following sub-steps: obtaining a pressure value of the soles of the intelligent shoes, and if the pressure value is less than a first pressure value, obtaining second inclination angles of the soles of the intelligent shoes, wherein the first pressure value of the intelligent shoes is obtained when the human wearing the intelligent shoes stands; and
   if at least one of the second inclination angles of the soles of the intelligent shoes is out of the preset inclination angle range,
   and the intelligent shoes have a continuous movement acceleration in an original direction within a third preset time, confirming that the human wearing intelligent shoes is in an accidental tumbling state.

3. The accidental tumbling monitoring method according to claim 1, wherein Step 1 further comprises the following sub-steps:
   obtaining direction data and acceleration data of the intelligent shoes, and then sending the direction data, the acceleration data and the first inclination angle to the monitoring platform to be recorded; and
   simulating a dynamic model by the monitoring platform according to the direction data, the acceleration data and the first inclination angle received by the monitoring platform.

4. The accidental tumbling monitoring method according to claim 1, wherein Step 3 comprises the following sub-step:
   obtaining image data around the intelligent shoes, and then sending the image data to the guardian.

5. An accidental tumbling monitoring system, comprising a first acquisition module, a first determination module and a first processing module;

the first acquisition module is used for obtaining, when receiving information that a human wearing intelligent shoes is in an accidental tumbling state, a first inclination angle of soles of the intelligent shoes and positioning information;

the first determination module is used for determining whether or not the first inclination angle is restored to a preset inclination angle range within a first preset time range;

the first processing module comprises a first communication unit, a first acquisition unit and a second communication unit;

the first communication unit is used for sending the positioning information to a guardian if the first inclination angle is not restored to the preset inclination angle range within the first preset time range, and a monitoring platform sends first aid information to an emergency center if not receiving feedback information from the guardian within a second preset time range;

the first acquisition unit is used for obtaining a speed value of the intelligent shoes if the first inclination angle is restored to the preset inclination angle range within the first preset time range;

the second communication unit is used for sending the positioning information to the guardian if the speed value is less than a preset speed threshold.

6. The accidental tumbling monitoring system according to claim 5, wherein the first acquisition module particularly comprises a second acquisition unit, a third acquisition unit and a confirmation unit;

the second acquisition unit is used for obtaining a pressure value of the soles of the intelligent shoes;

the third acquisition unit is used for obtaining second inclination angles of the soles of the intelligent shoes if the pressure value is less than a first pressure value, wherein the first pressure value of the intelligent shoes is obtained when the human wearing the intelligent shoes stands;

the confirmation unit is used for conforming that the human wearing the intelligent shoes is in an accidental tumbling state when at least one of the second inclination angles of the soles of the intelligent shoes is out of the preset inclination angle range and the intelligent shoes have a continuous movement acceleration in an original direction within a third preset time range.

7. The accidental tumbling monitoring system according to claim 5, wherein the first acquisition module further comprises a fourth acquisition unit and a third communication unit:

the fourth acquisition unit is used for obtaining direction data and acceleration data of the intelligent shoes;

the third communication unit is used for sending the direction data, the acceleration data and the first inclination angle to the monitoring platform to be recorded;

the accidental tumbling monitoring system further comprises the monitoring platform used for simulating a dynamic model according to the received direction data, acceleration data and first inclination angle.

8. The accidental tumbling monitoring system according to claim 5, wherein the first processing module comprises a fifth acquisition unit and a fourth communication unit;

the fifth acquisition unit is used for obtaining image data around the intelligent shoes;

the fourth communication unit is used for sending the image data to the guardian.

9. An accidental tumbling monitoring terminal, comprising intelligent shoes, wherein gyro sensors, speed sensors, processors, positioning devices and communication devices are arranged in the intelligent shoes, and the gyro sensors, the speed sensors, the positioning devices and the communication devices are connected to the processors;

the gyro sensors are used for obtaining, when receiving information that a human wearing the intelligent shoes is in an accidental tumbling state, a first inclination angle of soles of the intelligent shoes;

the speed sensors are used for obtaining a speed value of the intelligent shoes if the first inclination angle is restored to a preset inclination angle range within a first preset time range;

the positioning devices are used for obtaining, when receiving the information that the human wearing the intelligent shoes is in an accidental tumbling state, positioning information of the soles of the intelligent shoes;

the processors are used for determining whether or not the first inclination angle is restored to the preset inclination angle range within the first preset time range;

the communication devices are used for sending the positioning information to a guardian if the first inclination angle is not restored to the preset inclination angle range within the first preset time range.

10. The accidental tumbling monitoring terminal according to claim 9, wherein cameras connected to the processors are further arranged in the intelligent shoes and are used for obtaining image data around the intelligent shoes and sending the image data to the guardian.

* * * * *